United States Patent
Bartorelli

(10) Patent No.: US 7,423,063 B2
(45) Date of Patent: Sep. 9, 2008

(54) CALCIUM SALTS WITH CYTOTOXIC ACTIVITY

(75) Inventor: Alberto Bartorelli, Crans sur Sierre (CH)

(73) Assignee: Eureon AG, Freiburg (DE)

( * ) Notice: Subject to any disclaimer, the term of this patent is extended or adjusted under 35 U.S.C. 154(b) by 338 days.

(21) Appl. No.: 10/483,285

(22) PCT Filed: Jul. 1, 2002

(86) PCT No.: PCT/EP02/07222

§ 371 (c)(1),
(2), (4) Date: May 7, 2004

(87) PCT Pub. No.: WO03/006031

PCT Pub. Date: Jan. 23, 2003

(65) Prior Publication Data

US 2004/0180956 A1 Sep. 16, 2004

(30) Foreign Application Priority Data

Jul. 12, 2001 (IT) .......................... MI2001A1495

(51) Int. Cl.
*A61K 31/19* (2006.01)
(52) U.S. Cl. ..................................... 514/557
(58) Field of Classification Search ................. 514/557
See application file for complete search history.

(56) References Cited

U.S. PATENT DOCUMENTS

| 4,636,564 | A | * | 1/1987 | Baker | 546/289 |
| 5,250,545 | A | * | 10/1993 | Tsuruoka et al. | 514/328 |
| 5,593,987 | A | * | 1/1997 | Cullinan et al. | 514/217.03 |
| 5,610,166 | A | * | 3/1997 | Singh | 514/324 |
| 5,639,787 | A | * | 6/1997 | Riordan et al. | 514/474 |

FOREIGN PATENT DOCUMENTS

EP 0 305 083 * 3/1989

OTHER PUBLICATIONS

Webb, T.E. et al.:, "Pharmacokinetics relevant to the anticarcinogenic and anti-tumor activities of glucarate and the synergistic combination of glucarate: retinoid in the rat" Biochemical Pharmacology, vol. 47, No. 9, 1994, pp. 1655-1660, XP008009071 abstract.
Dwivedi, CH. et al.:, "Modulation of chemically initiated and promoted skin tumorigenesis in CD-1 mice by dietary glucarate", Journal of Environmental Pathology, Toxicological Oncology, vol. 9, No. 3, 1989, pp. 253-259, XP008009073, abstract.

* cited by examiner

*Primary Examiner*—Ardin H. Marschel
*Assistant Examiner*—Shirley V Gembeh
(74) *Attorney, Agent, or Firm*—Young & Thompson

(57) ABSTRACT

Calcium salts, in particular calcium trifluoroacetate, are added to medicaments to provide cytotoxic and antitumoral activity. The medicaments can be administered to cancer patients as part of a method of treating a cancer patient. The medicaments can also be applied to a tumor to treat the tumor. The medicaments may be administered or applied orally or parenterally.

15 Claims, No Drawings

CALCIUM SALTS WITH CYTOTOXIC ACTIVITY

The present invention relates to the use of calcium salts, in particular calcium trifluoroacetate, to prepare medicaments with cytotoxic and antitumoral activity.

Calcium salts, in particular calcium gluconate, have been used for some time in human medicine to treat osteoporosis and all conditions in which an increase in the blood calcium level is indicated. The use of calcium salts to treat tumoral and hyperproliferative disorders has not been described to date; however, possible chemoprotective effects have been postulated for some calcium salts, in particular calcium glucarate.

It has now been found that some calcium salts, in particular calcium trifluoroacetate, have a surprising cytotoxic activity which is selective for tumour cells. This activity has been demonstrated on cell line cultures of human and murine tumours of various origins (colon, lung, pancreas, breast, prostate, liver, stomach and ovaries) such as HT 29, Kato, C-26, H G C 27 and PA-1 cells.

Calcium trifluoroacetate, prepared with conventional methods from trifluoroacetic acid and calcium oxide or hydroxide, and added to each well (~10,000 cells) in an aqueous solution in quantities ranging between 0.001 and 1.5 mg, causes the death of 90-95% of tumour cells or more. Under the same conditions, normal human cell lines proved almost insensitive or at least considerably less sensitive to the cytotoxic effect attributable to calcium trifluoroacetate. Similar effects have been obtained with other calcium salts of pharmaceutically acceptable acids, such as acetate, nitrate, chloride and the like, though to a lesser extent. However, trifluoroacetate seems to be preferable in view of its favourable toxicological properties.

For use in the treatment of tumours, calcium trifluoroacetate or other calcium salts will preferably be administered parenterally, for example by the intramuscular, intravenous or subcutaneous route, at doses ranging between 0.1 and 10 mg/kg/day. For this purpose, the calcium salt will be suitably formulated in the form of sterile suspensions or solutions, possibly with the aid of conventional vehicles or solvents. However, other administration routes would also be possible, such as the oral route or topical infusion at the site of the tumour lesion. Calcium salts, and in particular calcium trifluoroacetate, can be used in combination with other antitumoral drugs which have complementary, synergistic or otherwise useful activity.

Other disorders in which antiproliferative activity or control of cell growth is indicated can also be treated in addition to tumours.

The results of experiments carried out with calcium trifluoroacetate are set out below.

Toxicity in Mouse and Rat

Calcium trifluoroacetate, administered at the acute dose of 200 mg/kg to Balb/c mice by the intraperitoneal route, does not produce any noteworthy toxic effects.

Four weeks' sub-chronic treatment at the dose of 100 mg/kg, again by the intraperitoneal route, did not cause any pathological effects. A similar 4-week treatment by the subcutaneous route was well tolerated at the dose of 10 mg/kg.

In Sprague Dawley rats, toxic effects were not observed after acute or sub-acute administration of 200 mg/kg of calcium trifluoroacetate by the intravenous route.

In Vitro Cytotoxicity

The cytotoxicity of calcium trifluoroacetate has been determined on 13 cell lines of malignant human tumours and 4 lines of benign tumours.

20 µl of $Ca(CF_3COO)_2$ solutions at concentrations of 100, 50, 37.5, 25, 15, 12.5, 10 and 6.25 mg/ml are added to 96-well plates, each containing 10,000 cells/well in 100 µl of culture medium.

They are left overnight at 37° C., after which 40 µl of MTT (dimethylthiazole-0.2 g/100 ml PBS) is added, and they are left for 4 hours at 37° C.

After aspiration, 100 µl of SDS is added and they are left at 37° C. for 1 hour. The plate is read at 540 nm and 690 nm.

The toxicity of the sample is evaluated as the ratio between the absorbance value in the well with the treated cells and the absorbance value in the well with the control cells.

$$1 - \frac{\text{Absorbance of cells + sample}}{\text{Absorbance of control cells}} \times 100 = \% \text{ dead cells}$$

The MTT test is a quantitative calorimetric method that measures only live cells, because the mitochondrial enzymes of live cells are able to transform MIT tetrazolium salts into insoluble formazan.

The results are summarised in Table 1.

TABLE 1

Biological activity of $Ca(CF_3COO)_2$ in vitro

| CELL LINES | Concentration of $Ca(CF_3COO)_2$ in vitro (µg per well) | | | | | | | |
|---|---|---|---|---|---|---|---|---|
| | 2000 | 1000 | 750 | 500 | 300 | 250 | 200 | 125 |
| HEP G-2 | 100 | 83 | 75 | 68 | 37 | 29 | 18 | 17 |
| MG 63 | 100 | 93 | 74 | 60 | 53 | 45 | 32 | 27 |
| HGC-27 | 100 | 94 | 94 | 85 | 76 | 54 | 33 | 24 |
| A-172 | 100 | 83 | 70 | 60 | 58 | 47 | 32 | 25 |
| PSN-1 | 100 | 95 | 94 | 94 | 92 | 92 | 91 | 86 |
| C-26 | 100 | 88 | 88 | 87 | 80 | 70 | 55 | 47 |
| DU-145 | 85 | 78 | 77 | 67 | 65 | 50 | 33 | 22 |
| KATO | 94 | 84 | 70 | 59 | 52 | 35 | 29 | 7 |
| *CHANG* | *41* | *33* | *33* | *27* | *25* | *19* | *16* | *11* |
| *NCTC* | *36* | *34* | *32* | *30* | *25* | *22* | *19* | *19* |
| MCF-7 | 42 | 41 | 25 | 24 | 23 | 22 | 7 | 7 |
| T47D | 48 | 44 | 41 | 37 | 34 | 31 | 30 | 28 |
| FTC-238 | 82 | 77 | 75 | 63 | 35 | 25 | 20 | 13 |
| *W-138* | *82* | *76* | *67* | *52* | *48* | *34* | *31* | *23* |
| *CCD-8LU* | *55* | *42* | *39* | *32* | *15* | *5* | *4* | *0* |
| PA-1 | 100 | 100 | 100 | 98 | 97 | 96 | 70 | 52 |
| HT-29 | 95 | 89 | 76 | 69 | 60 | 50 | 47 | 32 |

Normal type: malignant cell lines
Bold italic type: benign cell lines

RESULTS

Malignant human cell lines of different histological types and origins demonstrate that the cytotoxic response to calcium trifluoroacetate differs between the various lines but, depending on dose, always reaches very high cell death levels: 8/14 reached 100% mortality, and 6/14 reached values ranging between 80% and 90%.

These results were obtained after 24 hours' incubation. Checks were performed after 6 hours in view of the possibly rapid turnover of the salt due to its very low molecular weight.

The data collected demonstrate that antitumoral activity takes place in a short time at low concentrations. If the concentration is increased, a non-specific toxicity of the salt develops which explains its low toxicity towards normal cells at high doses.

Experimental Murine Tumours

Balb/C mice were inoculated with 25,000 cells/mouse of C26 (murine colon adenocarcinoma).

Four days after the inoculation, the animals were treated subcutaneously with 5 mg/kg of calcium trifluoroacetate. The control group received saline only. The treatment was given every day. The tumour diameter was measured with a caliper gauge. On the 20th day after the inoculation the animals were killed and the tumours removed and weighed. The results are set out in Table 2. The mean weight and mean size of the tumours in the control mice were four times greater than those of the treated group. The data relating to the onset of tumours were also significant: 100% for the controls as against 40% for the treated mice.

TABLE 2

IN VIVO TREATMENT OF BALB/C MICE WITH MURINE TUMOR C 26

| | SIZE OF TUMOR (cm) | | | | WEIGHT OF TUMOR (g) |
|---|---|---|---|---|---|
| | 13th day | 15th day | 18th day | 20th day | 20th day |
| CONTROL GROUP Saline | | | | | |
| 1 | 0.5 | 0.9 | 1.1 | 1.4 | 0.695 |
| 2 | 0.5 | 0.9 | 1.4 | 1.7 | 1.308 |
| 3 | 0.5 | 0.9 | 1.1 | 1.2 | 0.652 |
| 4 | N/A | 0.7 | 1.2 | 1.2 | 0.545 |
| 5 | N/A | 0.8 | 1.4 | 1.7 | 0.821 |
| MEAN, S.D | $0.3 \pm 0.27$ | $0.84 \pm 0.089$ | $1.24 \pm 0.15$ | $1.44 \pm 0.25$ | $0.8042 \pm 0.298$ |
| Treated group 5 mg/kg $Ca(CF_3COO)_2$ | | | | | |
| 1 | N/A | N/A | N/A | N/A | 0 |
| 2 | N/A | N/A | N/A | N/A | 0.01 |
| 3 | N/A | N/A | N/A | N/A | 0 |
| 4 | N/A | 0.3 | 0.8 | 0.9 | 0.438 |
| 5 | 0.6 | 0.8 | 1.1 | 1.2 | 0.7 |
| MEAN, S.D. | $0.12 \pm 0.268$ | $0.22 \pm 0.349$ | $0.38 \pm 0.53$ | $0.42 \pm 0.58$ | $0.2296 \pm 0.32$ |

Treatment of Spontaneously Occurring Canine Tumours

Experiments carried out on spontaneously occurring tumours in domestic animals, especially dogs, are considered a reliable model which is predictive of activity in man (D. M Vail et al., *Spontaneously occurring tumors in companion animals as models for drug development*. Anticancer drug development guide: preclinical screening, clinical trials and approval. Edited by B. Teicher Humana Press Inc., Totowa, N.J.). Tumours in pets are more similar than rodent tumours to human tumours in terms of size, cell kinetics and behaviour.

Six dogs suffering from mammary tumours and one dog with a malignant lymphoma were treated. The treatment was given intravenously at doses ranging between 100 and 10 mg/kg/day of calcium trifluoroacetate. Despite some variability among animals, depending on the onset of side effects, especially vomiting, the highest dose (100 mg/kg) was administered initially for one to three days, followed by the lowest dose (10 mg/kg) for a few days. The highest dose was then reintroduced, but only given twice a week. Some animals were always treated with the highest dose, but at a lower frequency (9-10 administrations in approx. 20 days).

Although the results are of a preliminary nature and were obtained on a limited number of animals, they demonstrate the considerable antitumoral efficacy of calcium trifluoroacetate. In fact, the experiments demonstrated:

1. A reduction in the main tumour mass of 20% to over 50% of its initial volume. This reduction was evident after the first few administrations, and peaked at the end of the treatment cycle used so far (generally 3 weeks).
2. The reduced volume was generally accompanied by other phenomena involving the tumour mass such as colliquative necrosis, loss of contact with the surrounding tissues (adhesions) and finally, encapsulation or rupture of the wall, with leakage of necrotic material to the exterior.
3. Arrested development of metastases and, in some cases, necrosis, and their disappearance (resorption or calcification).
4. $Ca(CF_3COO)_2$ proved totally safe even at daily intravenous doses of 100 mg/kg; the only side effect, observed in two animals, was vomiting immediately after administration of the drug, and a slight increase in temperature (not exceeding 1° C.).

The toxicity tests, performed by monitoring the liver and kidney function parameters and coagulation times with particular care, did not indicate any pathological modification of those parameters in the treated animals.

Clinical Cases

Calcium trifluoroacetate was administered subcutaneously at doses ranging between 10 and 200 mg a day to five patients aged 56 to 63 suffering from cancer of the breast (one case), colon (three cases) and womb (one case), at advanced state of disease and with diffuse metastasis. Except for one case of colon cancer which ended in the death of the patient due to the highly advanced state of the disease (all cases were treated on the basis of a compassionate protocol for obvious ethical reasons), the therapeutic response was surprising, both in objective terms (approx. 10 to 40% reduction in tumour mass, reduction or disappearance of ascites and metastatic nodes, and a reduction in tumour markers such as CA19.9 and alpha-fetoprotein) and in subjective terms (improved mood, reduction and disappearance of pain, and return to working and social life). Even in the case of the patient who died, a reduction in the tumour mass was observed, but the patient died due to aggravation of neoplastic cachexia and cardiorespiratory complications.

The invention claimed is:

1. A method of treating a patient having cancer comprising:
   administering to a patient in need thereof a sufficient amount of cytotoxic medicaments,
   wherein said cancer treated is selected from the group consisting of breast, colon, and womb, and
   said cytotoxic medicaments comprise calcium trifluoroacetate.

2. The method according to claim 1, wherein said cytotoxic medicaments are in the form of a pharmaceutical composition, wherein said pharmaceutical composition comprises said calcium trifluoroacetate, mixed with a suitable carrier.

3. The method according to claim 1, wherein said sufficient amount is between 0.1 mg/kg/day of calcium trifluoroacetate and 10 mg/kg/day of calcium trifluoroacetate.

4. The method according to claim 1, wherein said sufficient amount is between 0.1 mg/kg/day of calcium trifluoroacetate and 200 mg/kg/day of calcium trifluoroacetate.

5. The method according to claim 1, wherein said cytotoxic medicament is administered parenterally or orally.

6. The method according to claim 1, wherein said patient is a human.

7. A method of treating a tumor comprising contacting a tumor with an effective amount of calcium trifluoroacetate.

8. The method according to claim 7, wherein said calcium trifluoroacetate is administered as a pharmaceutical composition, said calcium trifluoroacetate being mixed with a suitable carrier.

9. The method according to claim 8, wherein said suitable carrier is suitable for oral or parenteral administration.

10. The method according to claim 7, wherein said calcium trifluoroacetate is administered by topical infusion at the site of said tumor.

11. The method according to claim 7, wherein said tumor is of a cell line selected from the group consisting of HT-29, KATO, C-26, HGC-27, and PA-1.

12. The method according to claim 7, wherein said tumor is of a cell line selected from the group consisting of HEP G-2, MG 63, A-172, PSN-1, and DU-145.

13. The method according to claim 7, wherein said effective amount is between 0.1 mg/kg/day of calcium trifluoroacetate and 200 mg/kg/day of calcium trifluoroacetate.

14. The method according to claim 7, wherein said tumor is found in the breast, colon or womb of a patient.

15. The method according to claim 7, wherein said patient is a human.

* * * * *